United States Patent [19]

Johnson et al.

[11] Patent Number: 5,021,567

[45] Date of Patent: Jun. 4, 1991

[54] 8-HYDROXYQUINOLINE CHELATING AGENTS

[75] Inventors: David K. Johnson, Vernon Hills; Steven J. Kline, Grayslake, both of Ill.

[73] Assignee: Abbott Laboratories, Abbott Park, Ill.

[21] Appl. No.: 100,390

[22] Filed: Sep. 24, 1987

[51] Int. Cl.$^5$ .................. C07D 403/06; C07D 403/02
[52] U.S. Cl. .................................... 540/470; 540/474; 546/169
[58] Field of Search ................. 540/470, 474; 546/169

[56] References Cited

U.S. PATENT DOCUMENTS

| | | | |
|---|---|---|---|
| 4,017,596 | 4/1977 | Loberg et al. | 424/1 |
| 4,181,654 | 1/1980 | Weitl et al. | 260/239 BC |
| 4,309,305 | 1/1982 | Weitl et al. | 252/631 |
| 4,421,654 | 12/1983 | Plueddmann | 210/698 |
| 4,442,305 | 4/1984 | Weitl et al. | 562/451 |
| 4,454,106 | 6/1984 | Gansow et al. | 424/1.1 |
| 4,500,494 | 2/1985 | Scher | 423/24 |
| 4,543,213 | 9/1985 | Weitl et al. | 260/239 BC |
| 4,671,958 | 6/1987 | Rodwell et al. | 424/85 |

FOREIGN PATENT DOCUMENTS

| | | |
|---|---|---|
| 83129 | 7/1983 | European Pat. Off. . |
| 97373 | 1/1984 | European Pat. Off. . |
| 174853 | 3/1986 | European Pat. Off. . |
| 1081169 | 3/1984 | U.S.S.R. ............................. 540/474 |

OTHER PUBLICATIONS

J. Med. Chem, 1987, 30, 1987–1900, Yamato et al., Synthesis and Antitumor Activity of Tropolone Derivatives.
Advanced Inorganic Chemistry, F. A. Cotton and G. Wilkinson, 4th Edition, pp. 71–73, 1980.
Harris et al., J. Amer. Chem. Soc., 101, 6097 (1979).
Jain et al., J. Amer. Chem. Soc., 89, 724 (1967).
J. Amer. Chem. Soc., 90, 519 (1968).
Rodgers et al., Inorgn. Chem., 26 1622 (1987).
Sundberg et al., J. Med. Chem., 17, 1304 (1974).
McAfee et al., J. Nucl. Med., 17, 480 (1976).
Moerlein et al., Int. J. Nucl. Med. Biol., 8, 277 (1981).
Hata et al., Bull. Chim. Soc. Japan, 45, 477 (1972).
Goldenberg et al., N. Eng. J. Med., 298, 1384–88 (1978).
Order et al., Int. J. Radiation Oncology Biol. Phys. 12, 277–81 (1986).
Buchsbaum et al., Int. J. Nucl. Med. Biol., vol. 12, No. 2, pp. 79–82 (1985).
Wang et al., Inorg. Chem. 28, 723 (1987).
Sim et al., Inorg. Chem. 17, 1288 (1978).
Wilson et al., J. Amer. Chem. Soc., 90, 6041 (1968).
Rosenberg et al., Biochemistry, 11, 3623–28 (1972).
Hwang and Wase, Biochim. Biophys. Acta, 512, 54–71 (1978).
Zittle, Advan. Enzyme. 12, 493 (1951).
Burnett et al., Biochem. Biophys. Res. Comm., 96, 157–62 (1980).
Zalcberg & McKenzie, J. Clin. Oncology, vol. 3, pp. 876–882 (1985).
Morrison et al., Proc. Nat. Acad. Sci. U.S.A., 81, 6851–55 (1984).
Porath and Olin, Biochemistry, 22, 1621–30 (1983).
DeRiemer et al., J. Med. Chem. 22, 1019–23, (1979).
Goodwin et al., J. Nucl. Med., 22, 787–92 (1981).
Haner et al., Arch. Biochem. Biophys., 231, 477–86 (1984).
Schultz and Dervan, J. Amer. Chem. Soc., 105, 7748–50 (1983).
Meares et al., Anal. Biochem., 142, 68 (1984).

Primary Examiner—David B. Springer
Attorney, Agent, or Firm—Daniel R. Curry

[57] ABSTRACT

The present invention provides linear, cyclic and trifurcate tri- and tetramine backbone multidentate chelating agents based on the 8-hydroxyquinoline chelating unit. The chelating agents may optionally be substituted with a substate reactive moiety and antibody-metal ion conjugates may be produced for in vivo diagnostic and therapeutic methods.

13 Claims, No Drawings

8-HYDROXYQUINOLINE CHELATING AGENTS

BACKGROUND

The present invention relates generally to compounds, termed ligands, which bind to metals in a very stable manner. Specifically, it relates to ligands which bind to metals with sufficient stability that the resulting ligand-metal complexes can remain intact in vivo. Such complexes find a variety of uses in medicine, of particular interest to this invention being their use in radiopharmaceutical applications when the metal atom is a radiation emitting or absorbing isotope. According to certain embodiments, the invention relates to bifunctional ligand molecules capable of binding metals to substrates such as antibodies and other proteins by means of a specific substrate reactive group having a phenyl ring which is meta or para substituted with a substrate reactive moiety. Antibody-metal ion conjugates may be produced for use in vivo diagnostic imaging methods as well as in therapeutic methods where the metal ions emit cytotoxic radiation.

Many factors influence the stability of ligand-metal complexes, including both characteristics inherent in the metal itself and characteristics related to the molecular structure of the ligand molecule. The properties of metal atoms, while they can vary widely from metal to metal, are generally not amenable to premeditated manipulations intended to enhance complex stability, with the result that ligand structure is the focus of efforts in the art to maximize the stability of such complexes. Ligand molecules known to the art and relevant to this invention are typically organic molecules of relatively low molecular weight (100-2,000 daltons) which may be either naturally occurring compounds or synthetic materials subject to premeditated design.

Certain design criteria for producing useful synthetic ligands are well known in the art. The nature of the chemical bond formed between a ligand and a metal can be thought of as involving a donation of a pair of electrons present on the ligand molecule or, in molecular orbital terms, as a molecular orbital formed by combining a filled orbital on the ligand with a vacant orbital on the metal atom. Those atoms in the ligand molecule which are directly involved in forming a chemical bond to the metal atom are thus termed the donor atoms and these generally comprise elements of Groups V and VI of the periodic table with nitrogen, oxygen, sulfur, phosphorus and arsenic being those most commonly employed.

An important criterion in designing synthetic ligand molecules is based on the finding that the stability of a metal complex formed with a ligand containing two donor atoms within the same molecule is generally greater than that of the corresponding complex formed with two separate ligand molecules, each containing only a single donor atom, even though the metal and the donor atoms are the same in each case. A second important design criterion, is based on the limitation that the stereochemistry of the ligand molecule must be such as to permit both donor atoms to bind to the metal atom without producing severe steric strain in the framework of the ligand molecule.

Ligand molecules that contain two or more donor atoms capable of binding to a single metal atom are termed chelating agents or chelators and the corresponding metal complexes are called chelates. The underlying thermodynamic phenomenon responsible for the enhanced stability obtained when two or more donor atoms are present in the same ligand molecule is called the chelate effect, as described in detail in F. A. Cotton and G. Wilkinson, Advanced Inorganic Chemistry, 4th edition, pp. 71-73, published in 1980. The number of donor atoms present in a given chelator is termed the denticity of that chelator, ligands possessing two donor sites being called bidentate, those with three donor sites, tridentate, and so forth. Although the foregoing example used the case of a bidentate ligand to illustrate the chelate effect, the effect also applies to ligands of higher denticity, up to the point at which the denticity of the chelator matches the maximum coordination number attainable by the particular metal atom.

The maximum coordination number of a metal atom is an intrinsic property of that atom, relating to the number of vacant orbitals that the atom possesses and hence the number of chemical bonds it is able to form. For a given metal atom in a given oxidation state, the maximum coordination number is largely invariant and, as a rule, cannot be altered by changing the nature of the ligands. When all of the available vacant orbitals have been used to form bonds to donor atoms in the ligand or ligands, the metal atom is said to be coordinatively saturated. In general, the maximum stability of a metal complex is thus achieved when the complex is formed using a multidentate chelator, the denticity of which is sufficient to coordinatively saturate the metal atom. It is therefore an object of this invention to provide multidentate chelators capable of producing coordinatively saturated complexes of radiopharmaceutically useful metals.

Coordinative saturation for most metals of the first and second transition series and for the group IIIb metals of particular interest to the present invention is generally achieved at a coordination number of six. Attempts in the art to design chelators which would form maximally stable complexes with these metals have thus centered on the development of ligands containing six donor atoms. Of particular interest to the art has been the development of hexadentate chelators forming highly stable complexes with the biologically important metal iron(III). These efforts have often involved a biomimetic approach, since the most stable iron(III) complexes presently known are those formed by naturally occurring chelators produced by a variety of microorganisms as part of their mechanism for obtaining iron from the environment. Such chelators are termed siderophores, the most stable of all metal complexes known to the art being the iron(III) complex of a siderophore called enterobactin, which has the structure:

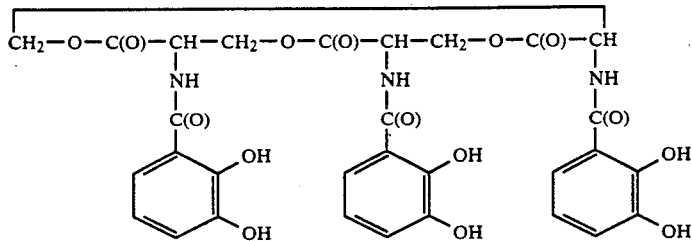

The formation constant of the ironenterobactin complex is $10^{52}$, as reported by Harris, et al., J. Amer. Chem. Soc., 101, 6097 (1979). Enterobactin binds to iron through the six phenolic oxygen atoms present on the three catechol moieties. Thus, the overall chelate structure is composed of three identical bidentate binding units, each unit comprising the structure

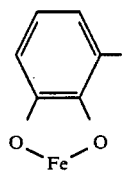

The remainder of the molecule functions as a framework which positions the three bidentate catechol moieties such that all three are stereochemically capable of binding to a single iron center.

A second powerful siderophore, which is used clinically to induce iron excretion, is called desferrioxamine B and has the structure

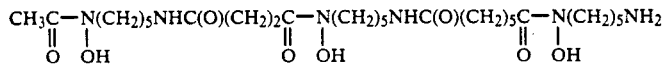

This chelator binds to iron through an array of six oxygen atoms present on three hydroxamate bidentate binding units, each unit having the structure:

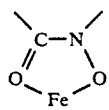

As is the case with enterobactin, the remainder of the molecule serves as a framework possessing sufficient steric flexibility to permit all three bidentate hydroxamate moieties to bind to the same iron atom.

Attempts in the art to mimic the foregoing siderophore structures have focused on the production of compounds employing synthetic frameworks to position the natural catecholate and hydroxamate moieties appropriately for formation of hexadentate chelates.

Harris, et al., disclose a synthetic hexadentate chelating compound 1,3,5-N,N',N''-tris(2,3-dihydroxybenzoyl)triamomethyl benzene (MECAM) wherein three catechol moieties are linked to a benzene backbone moiety.

Jain, et al., J. Amer. Chem. Soc., 89, 724 (1967) and J. Amer. Chem. Soc., 90, 519 (1968) disclose the use of the trifurcate tetraamine tris-(2-aminoethyl)amine (TREN) as a tetradentate chelator for metals such as copper and zinc.

Rodgers, et al., Inorg. Chem., 26, 1622 (1987) and references therein disclose the synthesis of a number of hexadentate tricatechol analogs of enterobactin including one utilizing TREN as a backbone. The compounds form very stable complexes with iron.

Weitl et al., U.S. Pat. Nos. 4,181,654, 4,309,305 and 4,543,213 disclose compounds comprising four 2,3-dihydroxybenzoic acid amide (catechol) moieties arranged about a cyclic or linear azaalkane framework. The dihydroxybenzoyl groups may optionally be substituted with a nitro group, a sulfonate group or a pharmaceutically acceptable sulfonate salt. The compounds are disclosed to be particularly useful for sequestering actinide (IV) ions by formation of octadentate complexes. Weitl, et al., U.S. Pat. No. 4,442,305 relates to polybenzamide compounds of lower denticity comprising two 2,3-dihydroxy benzoyl groups linked by an azaalkane framework. Such quatradentate compounds are also said to be useful for sequestering actinide (IV) ions according to both in vivo and in vitro procedures.

Of interest to the present invention is art relating to chelating agents utilizing atoms other than oxygen as electron donors. The polyaminopolycarboxylate chelators such as ethylenediaminetetraacetic acid (EDTA) and diethylenetriaminepentaacetic acid (DTPA), which are well known in the art and form stable complexes with a wide range of metals, derive much of their utility from the fact that they present a combination of both oxygen and nitrogen donors. The synthesis of bifunctional DTPA and EDTA analogues is well known. Sundberg, et al., J. Med. Chem., 17, 1304 (1974) discloses the synthesis of bifunctional EDTA derivatives characterized by the attachment of unique protein substrate reactive functions such as paraaminophenyl protein reactive substituents at a methylene carbon of the polyamine backbone.

Of interest to the present invention are disclosures relating to 8-hydroxyquinoline, also known as oxine, a bidentate binding unit containing both an oxygen donor atom and a nitrogen donor atom which has the structure shown below when bound to a metal atom, M

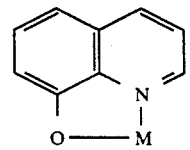

As is well known in the art, 8-hydroxyquinoline forms complexes with a wide range of metals and is known for use in extraction of various metal ions from solutions. See, Plueddemann, U.S. Pat. No. 4,421,654 and Scher, U.S. Pat. No. 4,500,494, which discloses a variety of substituted oxines. 8-hydroxyquinoline is known to be particularly useful for complexing group IIIb metals. The latter are of particular interest to the present invention since the heavier group IIIb elements find wide use in nuclear medicine, especially the gamma emitting isotopes gallium-67, indium-111 and thallium-201 and the positron emitting metal gallium-68. McAfee, et al., J. Nucl. Med., 17, 480 (1976) discloses the labelling of blood cells with 8-hydroxyquinoline complexes of indium-111 and technetium-99m. Moerlein, et al., Int. J. Nucl. Med. Biol., 8, 277 (1981), discloses various linear and branched 2,3-dihydroxybenzoylamide analogs of enterobactin and their use with both gallium and indium as radiopharmaceuticals. The reference also discloses the use of indium-111 labelled 8-hydroxyquinoline. Loberg, et al., U.S. Pat. No. 4,017,596 disclosed the use of chelates of cobalt-57, gallium-67, gallium-68, technetium-99m, indium-111 and indium-113m with 8-hydroxyquinoline as radiopharmaceutical external imaging agents. Goedemans, et al., European Patent Application No. 83,129 discloses antibodies and antibody fragments labelled with radionuclides through bifunctional chelating agents including 8-hydroxyquinoline. The chelating agents of the references form complexes in which three 8-hydroxyquinoline ligands are bound to each metal atom.

While the tris(8-hydroxyquinoline) complexes are satisfactory for the foregoing applications, they are of limited utility as radiopharmaceuticals for in vivo use as the bidentate 8-hydroxyquinoline ligand has a formation constant for, for example, gallium of only $10^{14.5}$ whereas that of the serum protein transferrin is $10^{23.7}$. Consequently, once in the bloodstream, such complexes would tend to break down and release the radioactive metal to transferrin, resulting in undesirably high and persistent blood background levels of radioactivity.

Hata, et al., Bull. Chem. Soc. Japan, 45, 477 (1972) discloses azomethyl and azomethine derivatives of 8-hydroxyquinoline-2-carbaldehyde. One derivative is N,N'-Bis(8-hydroxy-2 quinolylmethyl)ethylene diamine comprising two 8-hydroxyquinoline chelating moieties attached to an ethylene diamine framework. The reference suggests that the tetradentate chelator may form more stable metal complexes than oxine as a consequence of its higher basicity.

Of interest to the present invention are disclosures showing the use of protein/metal ion conjugates for diagnostic and therapeutic purposes. Gansow, et al., U.S. Pat. No. 4,454,106 discloses the use of monoclonal antibody/metal ion conjugates for in vivo and in vitro radioimaging diagnostic methods. Goldenberg, et al., N. Eng. J. Med., 298, 1384–88 (1978) discloses diagnostic imaging experiments wherein antibodies to the known tumor associated antigen carcinoembryonic antigen (CEA) are labelled with 131iodine and injected into patients with cancer. After 48 hours, the patients are scanned with a gamma scintillation camera and tumors are localized by the gamma emission pattern.

Other workers disclose the therapeutic use of antibody/metal ion conjugates for delivery of cytotoxic radioisotopes to tumor deposits in vivo. Order, et al., Int. J. Radiation Oncology Biol. Phys., 12, 277–81 (1986) describes treatment of hepatocellular cancer with antiferritin polyclonal antibodies to which 90yttrium has been chelated. Buchsbaum, et al., Int. J. Nucl. Med. Biol., Vol. 12, No. 2, pp. 79–82, (1985) discloses radiolabelling of monoclonal antibodies to CEA with 88yttrium and suggests the possibility of localization and treatment of colorectal cancers therewith. Nicolotti, EPO Application No. 174,853 published March 19, 1986, discloses conjugates comprising metal ions and antibody fragments. According to that disclosure, monoclonal antibodies of subclass IgG are enzymatically treated to remove the Fc fragment and reductively cleave the disulfide bond linking the antibody heavy chains. The Fab' fragment is then linked to a chelating agent bound to a radionuclide metal ion for in vivo diagnostic or therapeutic use. Also of interest to the present application is the disclosure of Wang, et al., J. Nucl. Med., 28, 723 (1987), which relates to a bifunctional bidentate chelator derived from the naturally occurring 8-hydroxyquinoline derivative xanthurenic acid. This chelator has the structure

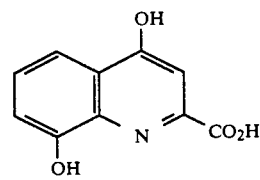

The carboxylic acid is converted to an N-hydroxysuccinimidyl ester, which reacts with the side chain amino groups of proteins to link the bidentate chelator to the substrate. The stability of a single bidentate unit tends to be insufficient for in vivo applications and the use of a complex containing three xanthurenic acid active ester ligands would generally be expected to lead to deleterious cross linking between proteins and concomitant denaturation of the protein substrate.

SUMMARY OF THE INVENTION

The present invention relates to compounds characterized by having the structure:

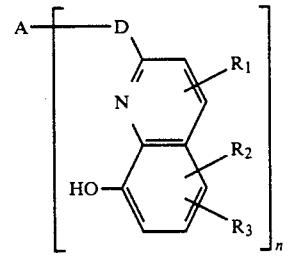

wherein D is selected from the group consisting of

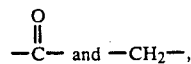

wherein $R_1$, $R_2$, and $R_3$ are the same or different and are selected from the group consisting of hydrogen, halogen, $C_1$–$C_3$ alkyl, nitro, nitroso, sulfonate and sulfonate-trialkyl ammonium salts, phenol, phosphate, $C_1$–$C_3$ carboxylic acid, carboxamide, sulfonamide, phosphonic acid and sulfate wherein n is 3 or 4 and wherein A is a linear, cyclic or trifurcate tri- or tetraamine wherein the amine nitrogens are linked by alkane, cycloalkane or ortho-substituted phenyl ring substituents having from 2 to 4 carbon atoms between amine groups, the amine nitrogens being positioned such that all of the attendant oxine units are capable of binding a single metal center wherein A may optionally be substituted at a methylene carbon by the group

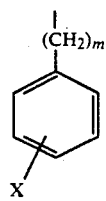

wherein X is meta or para and is nitro or a substrate reactive moiety and
wherein m = 0 to about 10.

Also provided by the invention are bifunctional chelating agents characterized by having the structure

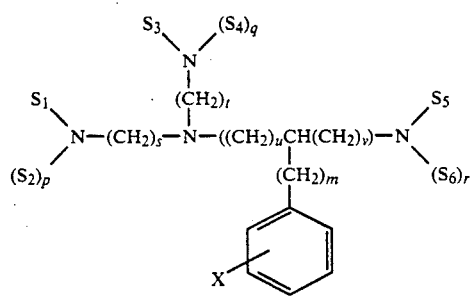

wherein m is 0 to about 10,
wherein p is 0 or 1,
wherein q is 0 or 1,
wherein r is 0 or 1,
wherein s is 2, 3 or 4,
wherein t is 2, 3 or 4,
wherein u is 0, 1, 2 or 3,
wherein v is 0, 1, 2 or 3, and
wherein u+v is 1, 2 or 3, and
wherein $S_1, S_2, S_3, S_4, S_5$ and $S_6$ are the same or different and are selected from the group consisting of
—H
—OH
—CH$_2$CO$_2$H
—CH$_2$CH$_2$CO$_2$H

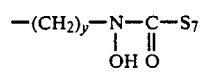

wherein
y is 1 to about 5,
and $S_7$ is aryl or $C_1$ to about $C_{20}$ alkyl,
and ring substituted or unsubstitued aromatic metal binding moieties selected from the group consisting of

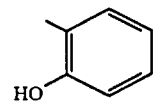

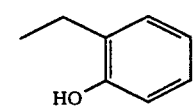

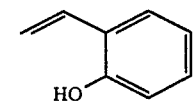

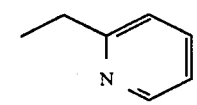

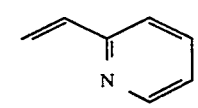

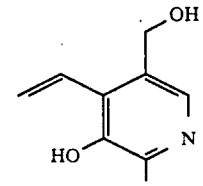

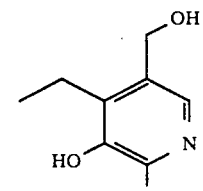

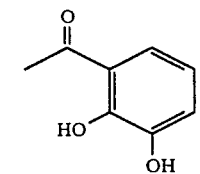

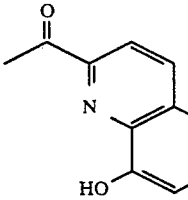

and

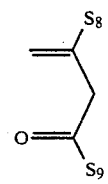

wherein $S_8$ and $S_9$ are the same or different and are $C_1$-$C_{20}$ alkyl or aryl, X is meta or para and is nitro or a substrate reactive moiety.

While the present invention provides numerous chelating agents of various sizes, shapes and denticities, there is no single preferred chelating agent according to the invention. Preferred compounds vary according to the specific nature of the metal ion to be bound.

The bifunctional chelating agents of the invention are suitable for binding metals including radioactive metal ions to a variety of substrate molecules including, but not limited to proteins, glycoproteins, peptides, poly(amino acids), lipids, carbohydrates, polysaccharides, nucleosides, nucleotides, nucleic acids, drugs, inhibitors and intact cells.

According to one aspect of the invention, antibody conjugates and antibody-metal ion conjugates are provided comprising the bifunctional chelating agents. In addition, the invention further provides in vivo diagnostic imaging methods utilizing radiation emitting and radiation absorbing metal ions. According to a further aspect of the invention, therapeutic methods are provided for treatment of conditions such as cancer whereby cytotoxic radiation emitting nuclides are bound to anti-tumor associated antigen antibodies by the chelating agents of the invention. The antibody-radionuclide conjugates according to the invention are then introduced into a subject and the cytotoxic radionuclides are selectively directed to cells bearing the tumor associated antigen. The compounds of the invention are also useful for in vivo therapeutic methods where it is desired to remove metal ions, particularly radioactive metal ions from the body, such as where subjects have been exposed to radioactive contamination.

DETAILED DESCRIPTION

The present invention relates to multidentate chelators based on the 8-hydroxyquinoline unit. Such chelators may be substituted and of various forms, and may be bifunctional comprising, in addition to chelating groups, a substrate reactive group including a substrate reactive moiety. Such bifunctional compounds which may be covalently bound to antibodies, other proteins and the like, are particularly useful for in vivo diagnostic and therapeutic purposes.

The present invention also provides bifunctional multidentate chelators based on the trifurcate tetraamine tris-(2-aminoethyl)amine (TREN). The tetraamine can be substituted at a methylene carbon with a substrate reactive group of the formula

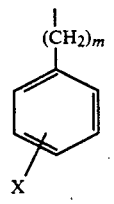

wherein X is nitro or a substrate reactive moiety and wherein m is 0 to about 10.

The parent tetraamine can itself function as a tetradentate chelator for metals such as copper and zinc as described by Jain, et al., J. Amer. Chem. Soc., 89, 724 (1967) and J. Amer. Chem. Soc., 90, 519 (1968). Bifunctional analogs of TREN may be covalently bound via the substrate reactive moiety to substrates including antibodies and other proteins.

Bifunctional chelating agents of higher denticity may be obtained by further derivatization of the TREN skeleton. Examples of compounds derived from the monofunctional TREN skeleton include imines formed by Schiff base condensation of TREN with salicylaldehyde or pyridine-2-carboxaldehyde, as described by Sim, et al., Inorg. Chem., 17, 1288 (1978) and Wilson, et al., J. Amer. Chem. Soc., 90, 6041 (1968), respectively. As another example, amides may be formed on acylation of the primary amines with chelating moieties, according to the methods of Rodgers, et al., Inorg. Chem., 26, 1622 (1987). A wide variety of metal binding moieties may be substituted onto the TREN arms. Such metal binding moieties include hydrogen, hydroxy, carboxymethyl, carboxyethyl and hydroxamate groups as well as aromatic and heterocyclic metal binding moieties. Such aromatic and heterocyclic metal binding moieties may be unsubstituted or may, like 8-hydroxyquinoline, be substituted with various substituents such as hydroxy and sulfonate at appropriate ring positions. The arms of the TREN molecule may be extended such that each arm comprises as many as four methylene carbons although for reasons of binding stability, it is generally preferred that there be only two or three methylene carbons in each arm.

Even while certain substituents and moieties of the chelating compounds of the invention are generally preferred, the specific structures of the compounds of the invention vary widely according to the natures of the substrate and the metal ion to be bound. Nevertheless, certain general principles may be applied to tailoring the compounds of the invention to specific uses. For example, certain metal ions such as members of the actinide and lanthanide series of metals have large radii and prefer high coordination numbers. Preferred chelating agents for binding with such ions are larger compounds with increased denticity. As another example, the precise location of particular amino acid residues in the structure of a protein (on or near an active site of an enzyme, or on or near the recognition region of an antibody), may require the selection of an alternative substrate reactive moiety on a chelating agent.

Most metal ions of interest are six coordinate or less and generally therefore are adequately bound by hexadentate compounds of the present invention (where n is 3). Nevertheless, some metal ions can have a higher coordinate character, including indium which can be 7-coordinate and yttrium which can be 8-coordinate, with the result that an octadentate chelator compound (wherein n is 4) may be particularly advantageous. It is unclear, however, whether higher denticity compounds (where n is 5 or greater) consistent with the teachings of the invention would provide any particular advantage because of the steric limitations on positioning five or more oxine substituents about a metal ion. Such steric limitations are of concern to the octadentate compounds of the invention and may limit substitution of the oxine rings on such compounds. Nevertheless, it is contemplated that particular advantages might be obtained by the linkage of two or more compounds of the present invention together in such a way that the resulting macrostructure is capable of binding to two or more metal ions simultaneously.

The quinoline compounds of the present invention preferably utilize 8-hydroxyquinoline binding functionalities. It is nevertheless contemplated that 8-mercaptoquinoline analogues may also be suitable for use according to the invention. While the nitrogen and oxygen (or sulfur) atoms on the oxine unit perform the metal binding function the other members of the double ring may be substituted. Such substitution does not generally affect the metal binding properties of the compounds provided it does not sterically interfere with binding. Substitution will, however, affect properties such as solubility which are critical to the utility of the compounds in various applications. Unsubstituted compounds according to the invention tend to have relatively poor solubility in aqueous solutions. It is therefore preferred that the oxine unit be substituted with hydrophilic moieties such as sulfonate which readily improve the solubility of the compounds. Consistent with these findings, $R_1$, $R_2$ and $R_3$ are preferably selected such that at least one of $R_1$, $R_2$ and $R_3$ is sulfonate and is substituted at the 4 or most preferably 5 position on the oxine ring.

The backbone A of the compounds is a linear, cyclic or trifurcate tri- or tetraamine wherein the amine nitrogens are linked by alkane, cycloalkane or ortho-substituted phenyl ring substituents having from 2 to 4 carbon atoms between amino groups, the amine nitrogens being positioned such that all of the attendant oxine units are capable of binding a single metal center. The backbone structure is limited by steric and thermodynamic constraints to those polyamines with from 2 to 4 carbon atoms between amine groups. Smaller backbones tend to be limited sterically and thus incapable of positioning the oxine units for binding to a metal center. Backbones with greater than 4 carbon atoms between amine groups tend to have low metal binding efficiencies as a consequence of the high amount of disorder (entropy) manifested in long oxine arms. The compounds of the present invention thus preferably have amine nitrogens linked by alkane substituents having from 2 to 4 carbon atoms and most preferably having 2 or 3 carbon atoms between amine groups. Three particularly preferred backbone structures are the residues of diethylenetriamine, 1,4,7-triazacyclononane, and tris (2-aminoethyl)amine (TREN):

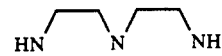

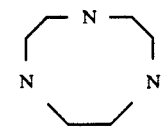

and

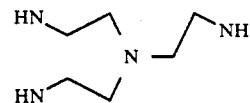

Particularly preferred compounds according to the invention include:

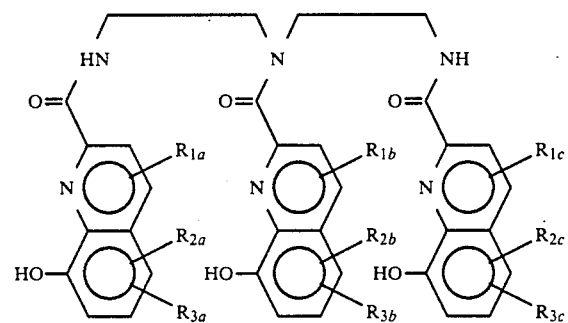

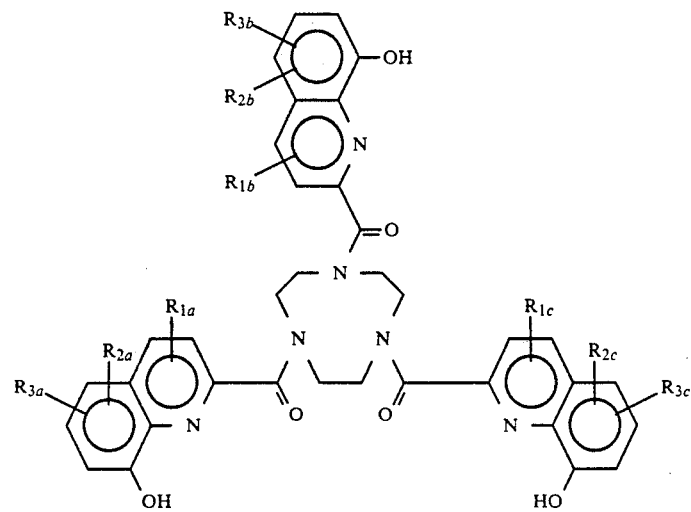

and

-continued

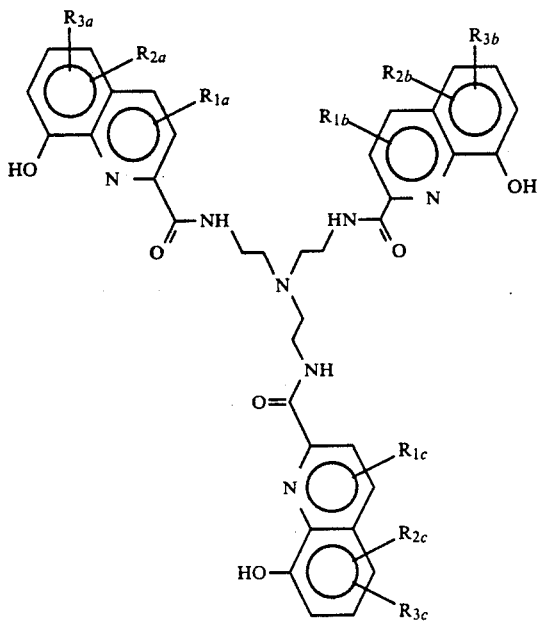

Substrate Reactive Moieties

The compounds according to the present invention may optionally include substrate reactive groups of the formula

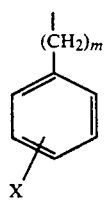

wherein m=0 to about 10 and is preferably 1. When X is nitro, it is understood that further conversion to a substrate reactive moiety is required prior to reaction with a substrate. Preferred substrate reactive moieties for X include those selected from the group consisting of:

| | |
|---|---|
| —NH$_2$, | (AMINO) |
| —NN$^+$, | (DIAZONIUM) |
| —NCS, | (ISOTHIOCYANATE) |
| —NCO, | (ISOCYANATE) |
| —NHNH$_2$, | (HYDRAZINE) |
| —NHCONHNH$_2$, | (SEMICARBAZIDE) |
| —NHCSNHNH$_2$, | (THIOSEMI-CARBAZIDE) |
| —NHCOCH$_2$Cl, | (CHLOROACETAMIDE) |
| —NHCOCH$_2$Br, | (BROMOACETAMIDE) |
| —NHCOCH$_2$I, | (IODOACETAMIDE) |
| —N$_3$, | (AZIDE) |
| —CO$_2$H | (CARBOXYLATE) |
| —NHCONH(CH$_2$)$_w$NH$_2$, | (AMINOALKYLUREA) |
| —NHCSNH(CH$_2$)$_w$NH$_2$, | (AMINOALKYL-THIOUREA) |
| —NHCONH(CH$_2$)$_w$CO$_2$H, | (CARBOXYALKYL-UREA) |
| —NHCSNH(CH$_2$)$_w$CO$_2$H, | (CARBOXYALKYL-THIOUREA) |

-continued

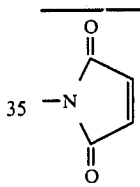 (MALEIMIDE)

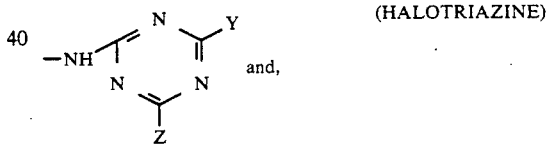 (HALOTRIAZINE)

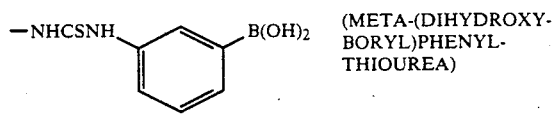 (META-(DIHYDROXY-BORYL)PHENYL-THIOUREA)

wherein Y is selected from the group consisting of Cl, Br and F;
wherein Z is selected from the group consisting of Cl, Br, F, OH and OCH$_3$; and
wherein w=1 to about 10.

Particularly preferred substrate reactive moieties include those wherein X is para substituted and is selected from the group consisting of: —NH$_2$, —NCS, —NHCOCH$_2$Br and —NHCSNH(CH$_2$)$_2$NH$_2$. Where it is desired to avoid direct linkage with the amino acid side chain of a protein substrate, preferred substrate reactive moieties include those which are capable of reaction with glycosylation present on some proteins. Because such glycosylation is generally inert, it must often be derivatized or oxidized to increase its reactivity. Substrate reactive moieties preferred for use in binding glycosylated proteins include —NHNH$_2$ and —NHCSNHNH$_2$.

Metal Ions

Metal ions which may be chelated according to the invention include gamma emitter isotopes which are useful for diagnostic scintigraphy. 111Indium with a half-life of 2.8 days is particularly useful while other suitable gamma emitters include $^{67}$gallium, $^{68}$gallium and $^{99m}$technetium. Materials according to the invention may be chelated to beta radiation emitters which are useful as cytotoxic agents for radiotherapy. Such emitters include isotopes such as $^{46}$scandium, $^{47}$scandium, $^{48}$scandium, $^{67}$copper, $^{72}$gallium, $^{73}$gallium, $^{90}$yttrium, $^{97}$ruthenium, $^{100}$palladium, $^{101m}$rhodium, $^{109}$palladium, $^{153}$samarium, $^{186}$rhenium, $^{188}$rhenium, $^{189}$rhenium, $^{198}$gold, $^{212}$radium and $^{212}$lead.

The chelating agents of the invention may also be used to bind alpha radiation emitting materials such as $^{212}$bismuth, positron emitters such as $^{68}$gallium and $^{89}$zirconium, fluorescent members of the lanthanide series of elements such as terbium and europium and of the transition series such as ruthenium and paramagnetic materials such as gadolinium and iron.

Complexing of Metal Ions

Methods for forming chelating agent/metal ion conjugates are well known to those of skill in the art. Complexes of the chelating agent and metal ions may generally be formed by incubation of the chelating agent/substrate conjugate with the metal ion in a buffered solution in which the conjugate is physiologically stable. Suitable buffers include those with weak metal-binding properties, such as citrate, acetate or glycine. Appropriate concentrations, temperatures and pH may be selected by one of skill in the art to ensure metal ions bind to the chelating functionality rather than weak metal binding sites on the substrates. It is particularly desired that all solutions be maintained free of metal impurities. After incubation for an appropriate period of time, unbound metal ions may be separated, if necessary, from the substrate/chelating agent/metal ion conjugate by a procedure such as gel filtration.

Substrate Reactive Functionalities

The substrate reactive moieties according to the present invention comprise those moieties capable of a specific binding reaction with at least one functionality present in a substrate molecule which may be a biologically active substrate. If the substrate is a protein, such moieties may be reactive with side chain groups of amino acids making up the polypeptide backbone. Such side chain groups include the carboxyl groups of aspartic acid and glutamic acid residues, the amino groups of lysine residues, the aromatic groups of tyrosine and histidine and the sulfhydryl groups of cysteine residues.

Carboxyl side groups presented by a substrate such as a polypeptide backbone may be reacted with amine substrate reactive groups of the compounds of the invention by means of a soluble carbodiimide reaction. Amino side groups presented by a substrate may be reacted with the isothiocyanate, isocyanate or halotriazine derivatives of this invention to effect linkage of the chelator to the polypeptide. Alternatively, amino side groups on the substrate may be linked to compounds of this invention bearing amine substrate reactive groups by means of bifunctional agents such as dialdehydes and imidoesters. Aromatic groups presented by a substrate may be coupled to the chelating agents of this invention via the diazonium derivative. Sulfhydryl groups on substrate molecules may be reacted with maleimides or with haloalkyl substrate reactive groups such as iodoacetamide. Free sulhydryl groups suitable for such reactions may be generated from the disulfide bonds of protein immunoglobulins or may be introduced by chemical derivatization. Linkage to free sulfhydryl groups generated in the intra-heavy chain region of immunoglobulins does not interfere with the antigen binding site of the immunoglobulin but may render the antibody incapable of activating complement.

When the substrate is a glycosylated protein, an alternative to forming a linkage to the compounds of the present invention via the polypeptide backbone is to form a covalent linkage with the carbohydrate side chains of the glycoprotein according to the methods such as those of Rodwell, et al., U.S. Pat. No. 4,671,958. Thus, the carbohydrate side chains of antibodies may be selectively oxidized to generate aldehydes which may then be reacted either with amine substrate reactive groups to form a Schiff base or with hydrazine, semicarbazide or thiosemicarbazide substrate reactive groups, to give the corresponding hydrazone, semicarbazone or thiosemicarbazone linkages. These same methods may also be employed to link the bifunctional chelators of this invention to non-proteinaceous substrates such as carbohydrates and polysaccharides.

An alternative substrate reactive moiety useful for linkage to carbohydrates and polysaccharides without the necessity for prior oxidation is the dihydroxyboryl moiety, such as is present in the meta(dihydroxyboryl)-phenylthiourea derivatives of the present invention. This moiety is reactive with substrates containing a 1,2-cis-diol, forming a 5-membered cyclic borate ester, and thus is of use with those carbohydrates, polysaccharides and glycoproteins which contain this group. The dihydroxyboryl derivatives may also be used to link the chelators of this invention to ribonucleosides, ribonucleotides and ribonucleic acids, since ribose contains a 1,2-cis-diol group at the 2',3' position, as disclosed by Rosenberg, et al., Biochemistry, 11, 3623–28 (1972). Deoxyribonucleotides and DNA substrates may not be linked to the present chelators in this fashion as the 3' hydroxyl group is absent. The latter substrates may, however, be conjugated to isothiocyanate derivatives of chelators by first forming an allylamine derivative of the deoxyribonucleotide as disclosed by Engelhardt, et al., EPO 97,373.

When the substrate to be linked with the chelators of this invention is an intact cell, either polypeptide-reactive or carbohydrate-reactive moieties may be employed. Hwang and Wase, Biochim. Biophys. Acta, 512, 54–71 (1978), disclose the use of the diazonium derivative of the bifunctional EDTA chelator of Sundberg, et al., J. Med. Chem., 17, 1304 (1974), to label erythrocytes and platelets with indium-111. The dihydroxyboryl moiety is reactive with a variety of bacteria, viruses and microorganisms, see Zittle, Advan. Enzyme., 12, 493 (1951) and Burnett, et al., Biochem. Biophys. Res. Comm., 96, 157–62 (1980).

According to the present invention, substrate reactive moieties include amino (—NH$_2$), diazonium (—NN$^+$), isothiocyanate (+NCS), isocyanate (—NCO), hydrazine (—NHNH$_2$), semicarbazide (—NHCONHNH$_2$), thiosemicarbazide (—NHCSNHNH$_2$), haloacetamide (—NHCOCH$_2$X) including chloro—, bromo— and iodoacetamide, azide (—N$_3$), carboxylate (—CO$_2$H), aminoalkylurea (—NHCONH(CH$_2$)$_w$NH$_2$), aminoalkylthiourea (—NHCSNH(CH$_2$)$_w$NH$_2$), carboxyalkylurea (—NHCONH(CH$_2$)$_w$CO$_2$H) and carboxyalkylthiourea (—NHCSNH(CH$_2$)$_w$CO$_2$H) wherein w is from 1 to about 10, maleimide, halotriazine including chloro—, bromo— and iodotriazine and meta-(dihydroxyboryl)-phenylthiourea (—NHCSNHC$_6$H$_4$B(OH)$_2$) Other reactive moieties which may be suitable for linking the chelating agents to substrates include disulfides, nitrenes, sulfonamides, carbodiimides, sulfonyl chlorides, benzimidates, —COCH$_3$ and —SO$_3$H. The preferred substrate reactive moiety for any particular application of this invention will be dictated by the nature of the substrate and by its susceptibility to loss of biological activity as a consequence of forming a given type of linkage. By definition, the formation of any given linkage involves a chemical transformation of the substrate reactive moiety, X, into the conjugated form of that moiety (hereafter the "residue" of X).

The reactive moieties of the invention are oriented at the meta or preferably para position on a phenyl group which is attached by means of an aliphatic spacer group to the chelating framework of the invention. The spacer group may consist of from one to about ten carbon atoms, and may be linear or branched alkyl or substituted alkyl provided such branching or substituents do not interfere with the metal binding sites or substrate reactive groups. Linear alkyl linkers are nevertheless preferred with C$_1$ alkyl linkers particularly preferred.

Substrates Useful With the Present Invention

Substrate molecules which may be reacted with the chelating agents of the present invention include proteins, glycoproteins, peptides, poly(amino acids), lipids, carbohydrates, polysaccharides, nucleosides, nucleotides, nucleic acids, drugs, inhibitors or intact cells. Suitable proteins include immunoglobulins, antigens, enzymes, components of the blood coagulation/anticoagulation system and various biochemically active molecules and receptors. Such proteins may be derived, for example, from genetically manipulated cells. According to one embodiment of the present invention, the bifunctional chelating agents may be used to bind various types of antibodies including IgA, IgD, IgE, IgG and IgM. The antibodies may be directed against a variety of antigenic determinants including those associated with tumors, histocompatibility and other cell surface antigens, bacteria, fungi, viruses, enzymes, toxins, drugs and other biologically active molecules. Antigens associated with tumors for which antibodies may be specifically reactive include such antigens as are described in Zalcberg and McKenzie, J. Clin. Oncology, Vol. 3; pp. 876-82 (1985) and include, but are not limited to, carcinoembryonic antigen (CEA), mucins such as TAG-72, human milk fat globule antigens and receptors such as the IL-2 and transferrin receptors. Such antibodies may be monoclonal or polyclonal or made by recombinant techniques such as described in Morrison, et al., Proc. Nat. Acad. Sci. U.S.A., 81, 6851-55 (1984).

Fragments of antibody molecules may also be bound including half antibody molecules and Fab, Fab' or F(ab')$_2$ fragments. Nicolotti, EPO 174,853 published March 19, 1986 hereby incorporated by reference, discloses methods by which entire antibodies are treated to effect a site specific cleavage of the two heavy chains, removing the F$_c$ portion at the carboxyl terminal ends of the heavy chains.

Substrates are reacted with the substrate reactive moieties of the chelating agents according to the methods disclosed above. Each substrate may be bound by more than one chelating agent as may be desired. The maximum extent of substitution on a substrate such as a protein, however, is limited by the nature of glycosylation on the protein or the number and location of reactive amino acid side chains on the molecule. Where, as with antibodies, it is desired that the conjugated protein retain its biological activity, the extent of substitution will be limited according to the nature and position of target glycosylation or amino acid residues both in the primary as well as in the tertiary sequence of the protein and their degree of involvement in the antigen binding site.

Other substrates contemplated by this invention include polysaccharide matrices which, when derivatized with chelators, provide means for the extraction of metals from metalloproteins and other metal containing substrates and for the affinity chromatography of proteins by the methods of Porath and Olin, Biochemistry, 22, 1621-30 (1983). Nucleic acids linked to the chelators of this invention may be used to monitor any nucleic acid hybridization reaction, as described by Engelhardt, et al., EPO 97,373. Bifunctional chelators linked to drugs may be used to follow the uptake of that drug into tissues, as exemplified by use of the antibiotic drug bleomycin linked to the bifunctional EDTA derivative of Sundberg, et al., J. Med. Chem., 17, 1304 (1974), as a means of imaging tumors, see DeRiemer, et al., J. Med. Chem., 22, 1019-23 (1979); Goodwin, et al., J. Nucl. Med., 22, 787-92 (1981). Intact cells, such as erythrocytes and platelets, have been labelled with radioisotopic metals by linkage to bifunctional chelators, as described by Hwang and Wase, Biochim. Biophys. Acta, 512, 54-71 (1978), and such labelled cells may be used to detect areas of abnormal accumulation in the body. Linkage of the compounds of this invention to low molecular weight substances which themselves undergo a specific binding reaction with a macromolecular biological molecule are contemplated. Haner, et al., Arch. Biochem. Biophys., 231, 477-86 (1984), disclose methods for linking EDTA to p-aminobenzamidine, a specific inhibitor of trypsin which binds strongly in the active site, providing an affinity label of use in probing that site. Schultz and Dervan, J. Amer. Chem. Soc., 105, 7748-50 (1983), disclose the sequence-specific double strand cleavage of DNA by iron complexes of conjugates formed by linking EDTA to distamycin, an N-methylpyrrole tripeptide which binds to DNA in a sequence-specific manner.

The following examples illustrate methods for synthesis of various chelating agents according to the invention. Examples 1 through 5 describe the synthesis of 2-carboxy-8-hydroxyquinoline and its sulfonated analogue 2-carboxy-5-sulfonato-8-hydroxyquinoline which are used to construct the multidentate chelating compounds of the present invention.

Examples 6 through 8 describe the synthesis of various hexadentate chelating agents according to the present invention. Example 6 describes the synthesis of Tris-N-(2-aminoethyl-[8-hydroxyquinoline-2-carboxamido]) amine, a trifurcate chelating agent. Example 7 describes the synthesis of N, N', N"-Tris(hydroxyquinoline -2-carboxamido)-1,4,7-Triazacyclononane, a cyclic hexadentate chelating agent. Example 8 describes the synthesis of N$^1$,N$^4$,N$^7$(tris-(8-hydroxyquinoline-2-carboxamido))diethylenetriamine, a linear hexadentate chelating agent according to the present invention.

Examples 9 through 13 describe the synthesis of a bifunctional TREN molecule with Example 13 describing the synthesis of $N^4$-[2-aminoethyl-2-(4-nitrobenzyl)-]diethylenetriamine tetrahydrochloride salt which is the tetrahydrochloride salt of bifunctional TREN. The bifunctional TREN molecule of Example 13 may be utilized as a bifunctional chelating agent itself or may be modified with various chelating moieties to produce other chelating agents.

Examples 14 through 16 describe the synthesis of various bifunctional analogues of the trifurcated hexadentate chelating agent of Example 6. The bifunctional analogues are synthesized from the tetrahydrochloride salt of bifunctional TREN produced according to Example 13. Such bifunctional chelating agents are capable of linking a metal ion to reactive moieties including antibodies and other proteins. Example 14 describes the synthesis of $N^4$-[2-aminoethyl -2-(4-nitrobenzyl)]Tris-N-(8-hydroxyquinoline-2-carboxamido)diethylenetriamine. Example 15 describes the synthesis of $N^4$-[2-aminoethyl-2-(4-aminobenzyl)]Tris-N-(8-hydroxyquinoline-2-carboxamido))diethylenetriamine dihydrochloride salt by conversion of the nitro moiety of Example 14 to an amino substrate reactive group. Example 16 describes the synthesis of $N^4$-[2-aminoethyl-2-(4-isothiocyanatobenzyl)]Tris-N-(8-hydroxyquinoline-2-carboxamido)diethylenetriamine hydrochloride salt by conversion of the amino moiety of Example 15 to an isothiocyanato substrate reactive group.

Example 17 describes the synthesis of Tris-N -(2-aminoethyl-[8-hydroxyquinoline-5-sulfanato-2-carboxamido]) amine, a sulfonated analogue of the trifurcated hexadentate chelating agent of Example 6. Example 18 describes the synthesis of an Indium complex of Tris-N-(2-aminoethyl-[8-hydroxyquinoline-2-carboxyamido]amine, the chelating agent according to Example 6. Example 19 describes the preparation of conjugates between the bifunctional chelating agent of Example 16 and a monoclonal antibody. Example 20 describes the preparation of radioactive metal ion complexes of Indium-111 with the antibody conjugates of Example 19.

EXAMPLE 1

8-Hydroxyquinoline-N-Oxide

In this example, 8-hydroxyquinoline-N-oxide was produced from 8-hydroxyquinoline. A stirred solution of 8-hydroxyquinoline (25.00 g, 172.2 mmol) in 550 ml of CHCl$_3$ was cooled to 0° C., and 3 -chloroperoxybenzoic acid (40.00 g, 80% Tech. grade ×0.231 mmol=0.185 mmol) was added slowly over 3 minutes. The solution was kept at 0° C. and stirred for 3 hours. During this period, the 3-chlorobenzoic acid byproduct precipitated. The 3-chlorobenzoic acid was removed by filtration and the orange filtrate was concentrated to dryness and the remaining solid was triturated with 2% NH$_4$OH (2×200 ml). The solid was isolated on a frit and washed with H$_2$O. The solid was dried in vacuo and was twice recrystallized from 10:1 hexane-acetone to give 8-hydroxyquinoline-N-oxide as light yellow needles, mp 138–39° C. (21.36 g, 132.7 mmol, 77% yield) $^1$H NMR (CDCl$_3$, TMS internal standard), δ 7.05 (d, J =7.5 Hz, 1 H), 7.22 (d, J =10.5 Hz, 1 H), 7.25 (t, J =7.5 Hz, 1 H), 7.48 (t, J =7.4 Hz, 1 H), 7.79 (d, J =9 Hz, 1 H), 8.25 (d, J =6.0 Hz, 1 H), note: phenol proton not seen. $^{13}$C NMR, δ 114.67, 116.65, 120.26, 129.54, 130.40, 132.08, 134.34, 153.79. MS for C$_9$H$_7$O$_2$N=161.16 g/mol, m/e 161 (M+, base peak), 116, 89, 63. IR 2248 m, 1560 s, 1530 m, 1470 m, 1280 s, 1189 m, 1156 m, 1049 m, 816 s.

EXAMPLE 2

8-Hydroxyquinoline-N-methoxy methyl sulfate

In this example, 8-hydroxyquinoline-N-methoxy methyl sulfate was produced according to a procedure wherein a stirred suspension of 8-hydroxyquinoline-N-oxide produced according to Example 1 (37.0 g, 229.6 mmol), in 750 ml of CCl$_4$ was brought to reflux under an atmosphere of argon. When the solution reached reflux, the rest of the 8-hydroxyquinoline had gone into solution and formed a yellow homogeneous solution. If the mixture was not homogeneous, then additional CCl$_4$ was added. Dimethyl sulfate (66.65 g, 528.4 mmol) was added to the refluxing solution and stirred at reflux for 8 hours. As the reaction proceeded, the desired product floated to the top of the reaction mixture The reaction was stopped when no more material separated from the mixture. The reaction mixture was allowed to cool to room temperature and the CCl$_4$ phase was decanted off. The remaining dark red tar was washed with dry diethyl ether and dried in vacuo for 48 hours to give 8-hydroxyquinoline-N-methoxy methyl sulfate as a microcrystalline deep orange solid (58.91 g, 89% yield). This material was extremely hydroscopic, and so additional purification was not attempted. $^1$H NMR (d$_6$-DMSO, TMS internal standard) δ 3.45 (s, 3 H), 4.46 (s, 3 H), 7.67 (d, J =9.00 Hz, 1 H), 7.89 (t, J=9.00 Hz, 1 H), 7.94 (d, J =6.00 Hz, 1 H), 8.14 (t, J=6.00 Hz, 1 H), 9.24 (d, J =9.00 Hz, 1 H), 9.76 (d, J=6.00 Hz, 1 H). MS for C$_{10}$H$_{10}$O$_2$N+SO$_4$CH$_3$=287.28 g/mol, (positive fast atom bombardment) (M+, base peak parent cation), 176, 190, 226, 256, 270, 289.

EXAMPLE 3

2-Cyano-8-hydroxyquinoline

In this example, 2-cyano-8-hydroxyquinoline was produced according to the following procedure. Sodium cyanide (30.11 g, 614.5 mmol) was dissolved in 150 ml of H$_2$O and cooled in an ice/NaCl bath to 0° C. 8-hydroxyquinoline-N-methoxy methyl sulfate produced according to Example 3 (58.91 g, 205.1 mmol), was dissolved in 250 ml of H$_2$O and gravity filtered through P5 filter paper. The 8-hydroxyquinoline-N-methoxy methyl sulfate solution was then added to the 0° C. stirred cyanide solution over a period of 2 hours. The mixture was stirred for an additional hour. The pH of the solution was lowered to pH 4.5 with concentrated acetic acid. This caused the desired material to precipitate as a grey solid. The material was isolated over a coarse frit and washed well with H$_2$O and dried in vacuo for 24 hours. The material was twice recrystallized from 10:1 hexane acetone to give 2-cyano -8-hydroxyquinoline (25.00 g, 146.9 mmol, 72% yield) as light brown needles, mp 132–43° C. $^1$H NMR (CDCl$_3$, TMS internal standard), δ 7.28 (d, J =6.0 Hz, 1 H), 7.41 (d, J =7.0 Hz, 1 H), 7.63 (t, J =6.0 Hz, 1 JH, 7.71 (d, J =7.0 Hz, 1 H), 7.9 (s, 1 H), 8.30 (d, J =8.0 Hz, 1 H). MS for C$_{10}$H$_6$O$_2$N=170.17 g/mol, m/e 171 (M+H, base peak), 162, 146, 188 (M+ +NH$_3$).

EXAMPLE 4

2-Carboxy-8-hydroxyquinoline

2-Cyano-8-hydroxyquinoline produced according to Example 3 (25.00 g, 146.9 mmol), was added to a stirred solution of 3 N NaOH (45.01 g in 375 ml of $H_2O$). The solution was refluxed for 5 hours, the reaction was stopped when base was no longer detectable at the top of the condenser by pH paper, and allowed to cool to room temperature. The pH of the reaction mixture was lowered to pH 4.5 with 5 N HCl. The desired product was then extracted into 2 L of ethyl acetate. The ethyl acetate solution was concentrated to dryness and taken up in 2 g fractions in methanol, 200 ml and applied to a Sephadex LH-20 column (750 g, methanol elution) for additional purification. The major fraction was isolated from the column and recrystallized from $H_2O$ to give 2-carboxy-8-hydroxyquinoline (20.10 g, 106.3 mmol, 72% yield) as bright yellow crystals, mp 215–216° C. $^1$H NMR ($d_6$-DMSO, TMS internal standard), δ 7.25 (d, J = 9.0 Hz, 1 H), 7.54 (d, J = 7.50 Hz, 1 H), 7.65 (t, J = 7.4 Hz, 1 H), 8.18 (d, J = 9.0 Hz, 1 H), 8.58 (d, J = 9.0 Hz, 1 H), 10.23 (broad s, 1 H). $^{13}$C NMR, δ 111.98, 117.56, 119.92, 129.89, 130.42, 136.43, 138.29, 144.23, 153.80, 165.10. MS for $C_{10}H_7O_3N$ = 189.17 g/mol, m/e (M+H, base peak), 190, 172, 162, 143, 116, 104, 89.

EXAMPLE 5

2-Carboxy-5-sulfonato-8-hydroxyquinoline

2-Carboxy-8-hydroxyquinoline produced according to Example 4 (1.00 g, 5.3 mmol), was dissolved in 20 ml of concentrated $H_2SO_4$ and heated to 100° C. with stirring for 4.5 hours. The mixture was allowed to cool to room temperature and left for 48 hours to slowly complete the reaction. To the solution was slowly added 150 ml of $H_2O$ and the resultant mixture was cooled to 5° C. Over the next 48 hours, the desired material crystallized out of solution to give 2-carboxy-5-sulfonato-8-hydroxyquinoline as dark orange hair like crystals (0.99 g, 3.7 mmol, 70% yield), mp>350° C. $^1$H NMR ($d_6$-DMSO, TMS internal standard), δ 7.11 (d, J = 9.0 Hz, 1 H), 8.01 (d, J = 7.5 Hz, 1 H), 8.22 (d, J = 9.0 Hz, 1 H), 9.42 (d, J = 9.0 Hz, 1 H), phenolic carboxylic and sulfonic acid protons not seen. $^{13}$C NMR, δ110.02, 120.02, 126.64, 128.82, 135.22, 136.68, 138.52, 144.09, 154.52, 165.33. MS for $C_{10}H_7O_6NS$ = 269.23 g/mol, m/e (M+H parent ion peak) 270, 226, 190, 146, 130.

EXAMPLE 6

Tris-N-(2-Aminoethyl-[8-hydroxyquinoline-2-Carboxamido]) Amine

2-Carboxy-8-hydroxyquinoline produced according to Example 4 (1.00 g, 5.3 mmol), was dissolved in 100 ml of dry tetrahydrofuran (THF). To the stirred solution was added N-hydroxysuccinimide (0.66 g, 5.7 mmol) and 1,3-Dicyclohexylcarbodiimide (1.16 g, 5.7 mmol). The reaction vessel was sealed with a septum and stirred at room temperature for 24 hours. The precipitated 1,3-dicyclohexylurea by-product was removed from the solution with filtration. To the resultant yellow solution was added tris-(2-aminoethyl)amine (0.25 g, 1.8 mmol) (TREN) through the septum and the solution was stirred for 48 hours. The solution was concentrated to dryness and taken up in 400 ml of ethyl acetate. The ethyl acetate phase was washed with $H_2O$ (1L) until no more N-hydroxysuccinimide could be detected by thin layer chromatography (silica, 90:10 $CH_2Cl_2$:$CH_3OH$). The organic phase was dried over $MgSO_4$, and concentrated to dryness. The resultant solid was dissolved in 175 ml $CH_3OH$ and applied to a 750 g Sephadex LH-20 column and eluted with $CH_3OH$. Tris-N-(2-aminoethyl-[8-hydroxyquinoline-2-carboxamido]) amine crystallized out of the appropriate fraction tubes after 72 hours as ultra fine white hair like crystals (.75 g, 1.14 mmol, 63% yield). $^1$H NMR ($d_6$-DMSO, TMS internal standard), δ 2.96 (t, J = 6.62 Hz, 6 H), 3.62 (q, J = 6.98 Hz, 6 H), 7.19 (d, J = 7.72 Hz, 3 H), 7.46 (d, J = 8.09 Hz, 3 H), 7.57 (t, J = 7.72 Hz, 3 H), 8.15 (d, J = 8.82, 3 H), 8.45 (d, J = 8.45 Hz, 3 H), 9.68 (t, J = 5.88 Hz, 3 H). $^{13}$C NMR, δ 37.49, 53.69, 111.37, 117.40, 118.65, 129.16, 129.30, 136.31, 137.46, 147.42, 153.45, 163.74. MS for $C_{36}H_{33}N_7O_6$ = 659.17 g/mol, (M+H base peak) 660, 458, 244, 215, 171, 144, 93.

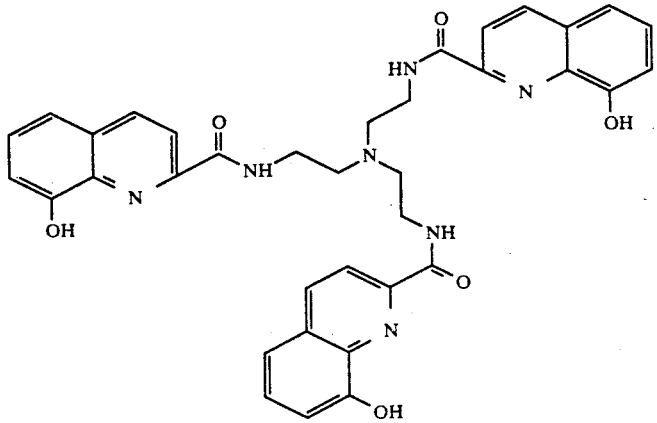

EXAMPLE 7

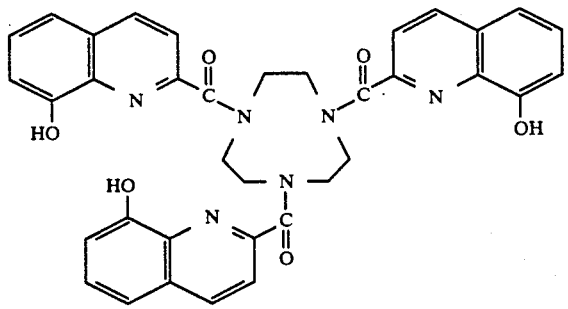

N,N',N''-Tris(8-hydroxyquinoline-2-carboxamido)-1,4,7-Triazacyclononane

A mixture comprising 2-carboxy-8-hydroxyquinoline produced according to Example 4 (0.38 grams, 1.98 mmole), and N-Hydroxysuccinimide (0.23 grams, 1.98 mmole) in DMF (5.5 ml) was stirred for 20 minutes before 1-(3-Dimethylaminopropyl)-3-ethylcarbodiimide·HCl (0.38 grams, 1.98 mmole) was added. After 24 hours at room temperature, 1,4,7-Triazacyclononane (0.08 grams, 0.62 mmole) (prepared by the method of Atkins, et al., Organic Syntheses, Vol. 58, 1978, pp. 86-97, John Wiley and Sons, New York) in DMF (2.0 ml) was added and the reaction mixture stirred for 7 days. The DMF was removed by evaporation under vacuum and the residue recovered was dissolved in $CH_2Cl_2$ (60 ml) and washed with $H_2O$ (3×60 ml). The organic layer was then dried with $Na_2SO_4$ and evaporated to dryness under vacuum. The crude residue was chromatographed on a Sephadex LH-20 column (bed -550 grams) eluting with methanol. 0.06 grams (15%) of N,N',N''-Tris(8-hydroxyquinoline-2-carboxamido)-1,4,7-Triazacyclononane was recovered as a white solid; mass spectrum, m/e 643 (M+H)+.

EXAMPLE 8

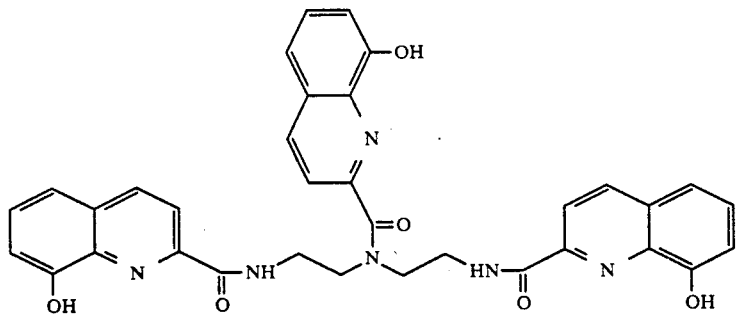

$N^1,N^4,N^7$(tris-(8-hydroxyquinoline-2-carboxamido))diethylenetriamine 2-carboxy-8-hydroxyquinoline produced according to Example 4 (1.00 g, 5.3 mmol) acid was dissolved in 100 ml of dry dimethylformamide (DMF). To the stirred solution was added N-hydroxysuccinimide (0.66 g, 5.7 mmol) and 1,3-dicyclohexylcarbodiimide (1.16 g, 5.7 mmol). The reaction vessel was sealed with a septum and stirred at room temperature for 24 hours. The precipitated 1,3-dicyclohexylurea by-product was removed from the solution with filtration. To the resultant yellow solution was added diethylenetriamine (0.18 g, 1.8 mmol) through the septum and the solution was stirred for 48 hours. The solution was concentrated to dryness and taken up in 400 ml of ethyl acetate. The ethyl acetate phase was washed with $H_2O$ (1 liter) until no more N-hydroxysuccinimide could be detected by thin layer chromatography (silica, 85:15 $CH_2Cl_2$:$CH_3OH$). The organic phase was dried over $MgSO_4$, and concentrated to dryness. The resultant solid was dissolved in 275 ml $CH_3OH$ and applied to a 750 g Sephadex LH-20 Column and eluted with $CH_3OH$. The desired product was isolated by removing the solvent from the appropriate fraction tubes as assessed by TLC (0.45 g, 0.729 mmol, 41% yield).

EXAMPLE 9

$N^1,N^7$-Bis(t-butoxycarbonyl)diethylenetriamine

To an ice bath cooled solution of THF (100 ml), diethylenetriamine (5.44 g, 52.73 mmol) and triethylamine (15.97 g, 157.84 mmol) was added. A solution of BOC-ON (2-(tert-butoxycarbonyloxyimino)-2-phenylacetonitrile), (26.0 g, 105.6 mmol) in 500 ml of THF was added dropwise over 45 minutes to the above solution. After 2 hours of stirring in the ice bath and 1 hour at room temperature, the solvent was removed in vacuo. The yellow/green oil remaining was dissolved in ethyl acetate (350 ml) and extracted with cold (5° C) 5% aqueous NaOH (5×200 ml). The organic layer was dried with $MgSO_4$ and concentrated to an oil. The oil was doubled in volume with 20% MeOH/80% $CH_2Cl_2$ and chromatographed on silica gel. Fractions were evaluated by TLC (10% MeOH/90% $CH_2Cl_2$, silica, ninhydrin). Product fractions were combined and dried in vacuo to a clear gum to give 11.5 g of $N^1,N^7$-bis(t-butoxycarbonyl)diethylenetriamine. Long term high vacuum treatment of the gum yielded a white crystalline solid, mp 69-71° C. $^1H$ NMR ($CDCl_3$, TMS internal standard), δ1.44 (s, 18H), 1.65 (bs, 2H), 2.71-2.75 (t,J =5.75 Hz, 4H), 3.19-3.25 (q,J =5.70 Hz, 4H), 5.07 (bs, 1H). $^{13}C$ NMR, δ28.19, 40.21, 48.74, 79.15, 156.13. MS for $C_{14}H_{29}N_3O_4$=303.4008 g/mol, direct chemical ionization; m/e 304 (M+, base peak), 248, 192, 173, 130. IR ($CDCl_3$), 3454m, 2980s, 2933m 1707s, 1505s, 1455m, 1392m, 1367s, 1270m, 1249m, 1170s, 1046m.

EXAMPLE 10

N-(t-Butoxycarbonyl)-4-Nitro-L-Phenylalanine-N-Hydroxysuccinimidyl Ester

N-t-BOC-para-nitro-L-phenylalanine (4.53 g, 4.59 mmol) was dissolved in 150 ml of ethyl acetate, to this solution was added N-hydroxysuccinimide (2.00 g, 17.39 mmol) and 1,3-dicyclohexylcarbodiimide (3.53 g, 17.11 mmol). The reaction flask was sealed with a septum and stirred at room temperature for 24 hours. The precipitated 1,3-dicyclohexylurea by-product was filtered off and the filtrate was concentrated to dryness. The white solid was recrystallized twice from 2-propanol (600 ml) to give the N-(t-butoxycarbonyl)-4-nitro-L-phenylalanine-N-hydroxysuccinimidyl ester as a white crystalline solid (4.92 g, 12.07 mmol, 82% yield). mp 178–79° C. $^1$H NMR (CDCl$_3$, TMS internal standard), δ1.44 (s, 9H), 2.89 (s, 4H), 3.25–3.50 (m, 2H), 5.01 (bs, 1H), 7.49 (d,J =9.00 Hz, 2H), 8.19 (d,J =9.00 Hz, 2H). MS for C$_{18}$H$_{21}$N$_3$O$_8$=407.3792 g/mol, direct chemical ionization; m/e 425 ((M+NH$_3$)$^+$, base peak), 408, 396, 352, 308, 265, 254, 163, 133.

EXAMPLE 11

N$^4$-[1-oxo-(2-aminoethyl-(N-t-butoxycarbonyl))-2-(4-nitrobenzyl)]-N$^1$,N$^7$-bis(t-butoxycarbonyl) diethylenetriamine N-(t-butoxycarbonyl)-4-nitro-L-phenylalanine -N-hydroxysuccinimidyl ester prepared according to Example 10, (3.0 g, 7.43 mmol) was dissolved in 150 ml of dry THF and to this solution N$^1$,N$^7$-bis(t-butoxycarbonyl)diethylenetriamine, prepared according to Example 9, (1.85 g, 6.09 mmol) was added. The flask was sealed with a septum and stirred at room temperature for 50 hours. The N-hydroxysuccinimide precipitate was filtered off and the filtrate was concentrated to dryness in vacuo to a clear gum. The gum was dissolved in 25 ml of methanol and applied to a Sephadex LH-20 column (750 g bed weight, 100% methanol, 5 ml/min.). The desired material was the first species off, as observed by TLC (silica, 40% EtOAc/60% CH$_2$Cl$_2$, R$_f$=0.2). The appropriate fractions were concentrated to dryness in vacuo to give a clear gum. The material was dissolved in 20 ml of CH$_2$Cl$_2$ and applied to a silica column for additional purification (100 g 60 mesh silica, 95% CH$_2$Cl$_2$, 15& MeOH, 10 ml/min.). Again by the same TLC system, the appropriate fractions were combined to give a clear amorphous solid, mp 60–62° C. (3.0 g, 5.04 mmol, 82% yield). $^1$H NMR (CDCl$_3$, TMS internal standard), δ1.38 (s, 9H), 1.42 (s, 18H, 3.30 (m, 4H), 3.28 (m, 2H), 3.35 (m, 4H), 4.98 (bs, 1H), 7.43 (d,J =9.0 Hz, 2H), 8.17 (d,J =9 Hz, 2H). MS for C$_{28}$H$_{45}$N$_5$O$_9$=595.6916 g/mol, direct chemical ionization (NH$_3$); m/e 596 ((M+H)$^+$, base peak), 540, 496, 484, 440, 384.

EXAMPLE 12

N$^4$-[1-Oxo-2-Aminoethyl-2-(4-Nitrobenzyl)]-Diethylenetriamine Tris Trifluoroacetate Salt N$^4$-[1-oxo-(2-aminoethyl-(N-t-butoxycarbonyl)) -2-(4-nitrobenzyl)]-N$^1$,N$^7$-bis(t-butoxycarbonyl) diethylenetriamine, prepared according to Example 11, (1.0 g, 1.67 mmol) was dissolved in 15 ml of trifluoroacetic acid under an atmosphere of argon. The solution was stirred at room temperature for 1 hour and concentrated in vacuo to a light yellow amorphous solid. The solid was redissolved in trifluoroacetic acid and the above procedure was repeated to assure complete removal of the t-butoxycarbonyl protecting group. The solid was dissolved in 20 ml of H$_2$O and freeze dried to give a light yellow solid (1.21 g, 1.61 mmol, 95% yield). $^1$H NMR (d$_6$-DMSO, TMS internal standard) δ 3.10–3.70 (m, 10H), 4.63 (s, 1H), 7.57. (d,J =9.0 Hz, 2H), 7.98 (bs, 1H), 8.07 (bs, 1H), 8.22 (d,J =9.0 Hz, 2H), 8.42 (bs, 1H). MS for C$_{21}$H$_{25}$N$_5$O$_{11}$F$_{12}$=751.436, free amine 295.1332, m/e 296 (M+, free cation, base peak), 278, 266, 223,182, 140, 104.

EXAMPLE 13

N$^4$-[2-Aminoethyl-2-(4-Nitrobenzyl)]Diethylenetriamine Tetra Hydrochloride Salt

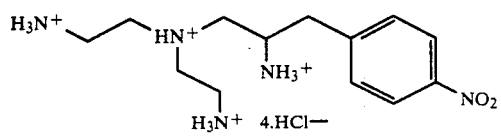

According to this example, the tetrahydrochloride salt of a bifunctional TREN (N$^4$-[2-aminoethyl-2-(4-nitrobenzyl)]diethylenetriamine tetrahydrochloride salt) was produced. N$^4$-[1-oxo-2-aminoethyl-2-(4-nitrobenzyl)]diethylenetriamine tris trifluoroacetate salt, prepared according to Example 12, (1.15 g, 1.53 mmol) was dissolved in 25 ml of dry THF and transferred to an ice bath cooled flask fitted with a condenser and under an atmosphere of argon. When the solution had reached ice bath temperature, 1.0 M borane -THF (22 ml, 0.304 g, 36.8 mmol) solution was added through the septum and stirred at 0° C. for one hour. The solution was then refluxed for 5.5 hours and recooled to 0° C. To this solution 20 ml of dry methanol was added. This step was carried out with caution because of the evolution of large amounts of gas. When the gas had stopped evolving from the solution, anhydrous HCl was bubbled through the septum for 1 minute, the solution was then refluxed for 1 hour. The flask was allowed to cool to room temperature and was concentrated to a light yellow solid in vacuo. This material was dissolved in a minimum amount of methanol and applied to a Sephadex LH-20 column (750 g, 100% methanol, 3 ml/min.). The desired material was first to elute off, the fractions were evaluated by TLC (silica, 40% NH$_4$OH/60% absolute ethanol, ninhydrin). The appropriate fractions were combined and were concentrated to dryness in vacuo to give the N$^4$-[2-aminoethyl-2-(4-nitrobenzyl)]diethylenetriamine tetra hydrochloride salt as a light yellow amorphous solid. (0.45 g, 1.05 mmol, 65% yield). $^1$H NMR (d$_6$-DMSO, TMS internal standard), δ 2.21–2.46 (m, 2H), 2.78–3.01 (m, 8H), 3.15–3.25 (m, 2H), 4.03 (bs, 1H), 7.66 (d,J =9.0 Hz, 2H), 8.20 (d,J =9.0 Hz, 2H). MS for C$_{13}$H$_{23}$N$_5$O$_2$·4HCl=427.20, free amine 281.15, m/e 282 (M+, free base, base peak) 265, 252, 239, 146, 126, 114, 104.

EXAMPLE 14

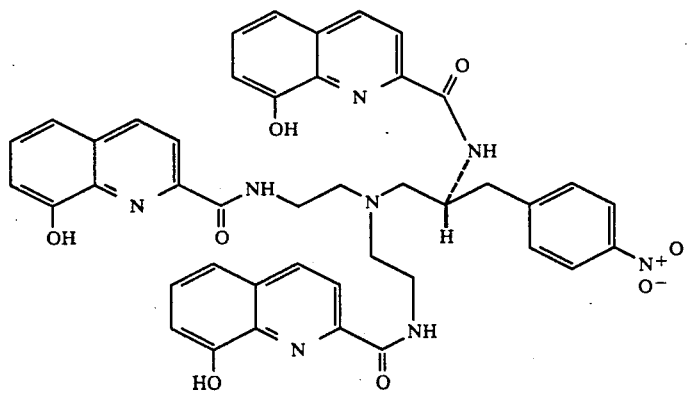

$N^4$-[2-Aminoethyl-2-(4-Nitrobenzyl)]Tris-N-(8-Hydroxyquinoline-2-Carboxamido)Diethylenetriamine 2-carboxy-8-hydroxyquinoline (0.985 g, 5.21 mmol), prepared according to Example 4, was dissolved in 100 ml of dry THF. To the stirred solution was added N-hydroxysuccinimide (0.650 g, 5.65 mmol) and 1,3 dicyclohexylcarbodiimide (1.150 g, 5.57 mmol). The reaction vessel was sealed with a septum and stirred at room temperature for 24 hours. The precipitated 1,3 -dicyclohexylurea by-product was removed from the solution with filtration. To the resultant yellow solution was added $N^4$-[2-aminoethyl-2-(4-nitrobenzyl)diethylenetriamine tetrahydrochloride, prepared according to Example 13, (0.250 g, .58 mmol) and 1 ml of triethylamine and the solution was stirred for 48 hours. The solution was concentrated to dryness and taken up in 400 ml of ethyl acetate. The ethyl acetate phase was washed with $H_2O$ (1 liter) until no more N-hydroxysuccinimide could be detected by thin layer chromatography (silica, 90% $CH_2Cl_2$/10% methanol). The organic phase was dried over $MgSO_4$, and concentrated to dryness. The resultant solid was dissolved in 175 ml of methanol and applied to a Sephadex LH-20 column (750 g bed weight, 100% methanol, 3 ml/min.). The fractions were analyzed by the above TLC system and the appropriate fractions were combined and concentrated to dryness in vacuo to give $N^4$-[2-aminoethyl-2-(4-nitrobenzyl)]tris-N-(8-hydroxyquinoline-2-carboxyamido)diethylenetriamine as a light yellow amorphous powder (0.300 g, 0.37 mmol, 64% yield). $^1$H NMR ($d_6$-DMSO, TMS internal standard, 70° C. $\delta$2.98-3.12 (M, 2H), 3.28-3-.37 (dd,J =15.0 Hz (geminal), J =3.0 Hz Iab), 2H), 3.49-3.63 (m, 4H), 3.64-3.75 (m, 4H), 4.50 (s, 1H), 7.13 (d,J =7.5 Hz, 3H), 7.30 (d,J =9.0 Hz, 2H), 7.38 (d,J =9 Hz, 1H), 7.39 (d,J =9Hz, 2H), 7.52 (t,J =8.0 Hz, 3H), 7.72 (d,J =9.0 Hz, 2H), 7.98 (d,J =9 Hz, 1H), 8.12 (d,J =9.0 Hz, 2H), 8.34 (d,J =8.5 Hz, 1H), 8.39 (d,J =9.0 Hz, 2H), 9.29 (d,J =10.5 Hz, 1H), 9.60 (t,J =6.0 Hz, 2H). MS for $C_{42}H_{38}N_7O_6NO_2$=794.8220 g/mol, direct chemical ionization ($NH_3$); m/e 795 ((M+H)$^+$, base peak), 765, 721, 706, 607, 581, 458, 446, 336. $^{13}$C NMR (very close doublets are seen due to rotomer barrier on many peaks) 37.152, 37.412, 48.996, 53.673, 59.218, 111,090, 116.985, 118.37, 122.237, 128.798, 128.87, 129.099, 129.296, 136.125, 136.214, 137.061, 145.364, 146.952, 147.301, 147.362, 153.344, 163.230, 163.627.

EXAMPLE 15

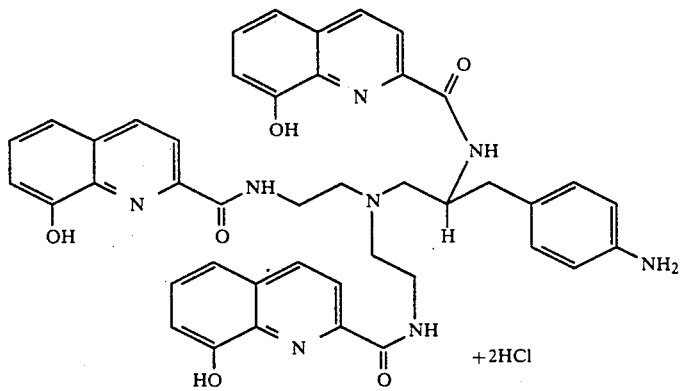

$N^4$-[2-Aminoethyl-2-(4-Aminobenzyl)]Tris-N-(8-Hydroxyquinoline-2-Carboxamido))Diethylenetriamine Dihydrochloride Salt $N^4$-[2-aminoethyl-2-(4-nitrobenzyl)]tris-N-(8-hydroxyquinoline-2-carboxamido))diethylenetriamine dihydrochloride salt (0.030 g, 0.03 mmol) prepared according to Example 14 was dissolved in 25 ml of $CH_3CN$. To this solution was added triethylamine (250 $\mu$l, 181.5 mg, 1.78 mmol) and dry formic acid (100 $\mu$l, 122.0 mg, 2.65 mmol). Pd on activated carbon (10 mg of 10% Pd on C by weight) was added to the solution, the suspension was then refluxed for 2.5 hours under an atmosphere of argon. The suspension was then allowed to return to room temperature. The Pd on carbon catalyst was removed by filtration and the filtrate was concentrated to dryness. The solid was suspended in 100 ml of 1N HCl and shaken for 5 minutes, the suspension was reduced in volume to 5 ml then isolated by lyophilization to yield the N$^4$-[2-aminoethyl-2-(4-aminobenzyl)]tris-N-(8-hydroxyquinoline-2-carboxamido))diethylenetriamine dihydrochloride salt as a amorphous light brown solid (0.024 g, 0.028 mmol, 95% yield). MS for $C_{43}H_{38}N_7O_6NH_2=764.8390$, direct chemical ionization (NH$_3$); m/e 765 ((M+H)$^+$, base peak), 563, 458, 429, 383, 350, 320, 305.

EXAMPLE 16

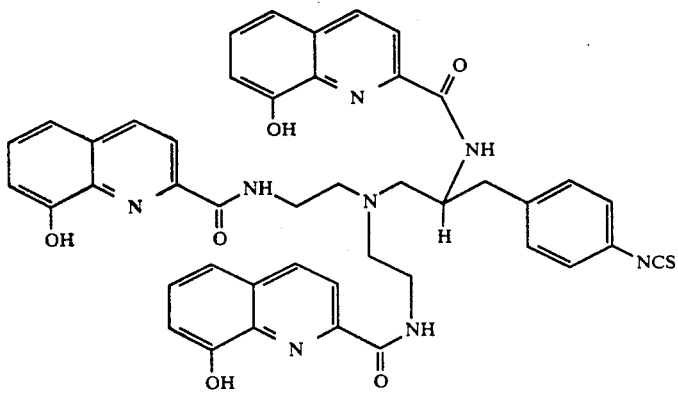

N$^4$-[2-Aminoethyl-2-(4-Isothiocyanotobenzyl)]Tris-N-(8-Hydroxyquinoline-2-Carboxamido)Diethylenetriamine Hydrochloride Salt N$^4$-[2-aminoethyl-2-(4-aminobenzyl)]tris-N-(8-hydroxyquinoline-2-carboxamido))diethylenetriamine hydrochloride salt (35.0 mg, 0.041 mmol) produced according to example 15 was dissolved in 20 ml of absolute ethanol. To this solution was added thiophosgene (6.4 ul, 9.6 mg, 0.082 mmol). The reaction flask was sealed with a septum and placed under an atmosphere of argon. The solution was stirred at room temperature for 3.5 hours, after which the solvent was removed in vacuo. This gave the desired product as a light brown amorphous solid (0.030 g, 0.037 mmol, 91% yield). MS for $C_{43}H_{38}O_6N_7.NCS.HCl=806.8942$ g/mol +HCl =843.3551 g/mol, positive fast atom bombardment, m/e 807 (M+, base peak parent cation), 837, 765, 718, 458, 244, 215, 185, 144.

EXAMPLE 17

Tris-N-(2-aminoethyl)-[8-hydroxyquinoline-5-sulfonato-2-carboxamido]) amine

2-Carboxy-5-sulfonato-8-hydroxyquinoline (0.500 g, 1.85 mmol) was dissolved in 100 ml of dry DMF. To the stirred solution was added N-Hydroxysuccinimide (0.225 g, 1.95 mmol) and 1,3 dicyclohexylcarbodiimide (0.405 g, 1.96 mmol). The reaction vessel was sealed with a septum and stirred at room temperature for 24 hours. The precipitated 1,3-dicyclohexylurea by-product was removed from the solution with filtration. To the resultant yellow solution was added tris(2-aminoethyl)amine (0.090 g, 0.619 mmol) through the septum and the solution was stirred for 48 hours at room temperature. The solution was concentrated to dryness and recrystallized twice from H$_2$O to give the desired product as a microcrystalline white solid (.365 g, 0.405 mmol, 65% yield). The desired product had improved solubility in aqueous solutions. $^1$H NMR (D$_6$-DMSO, TMS internal standard), δ 2.63 (m, 6H), 2.92 (m, 6H), 7.15 (d, J=9.0 Hz, 3H), 8.03 (d, J=9.1 Hz, 3H), 8.24 (d, J=9.1 Hz, 3H).

EXAMPLE 18

Indium Complex of Tris-N-(2-Aminoethyl-[8-Hydroxyquinoline-2-Carboxamido]Amine

Tris-N-(2-aminoethyl-[8-hydroxyquinoline-2-carboxamido]) amine (0.100 g, 0.151 mmol) produced according to Example 6 was dissolved with heating in CH$_3$CN (about 225 ml) to form a refluxing saturated solution, to

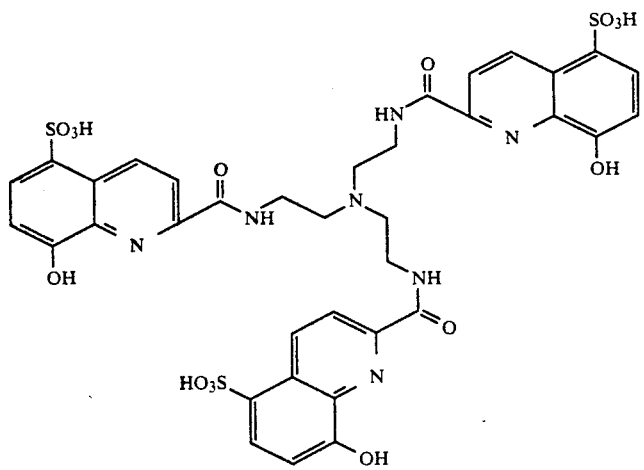

this solution was added triethylamine (85 μl, 0.065 g, 0.604 mmol). InCl₃ (0.035 g, 0.159 mmol) was dissolved in 35 ml of CH₃CN and was then added dropwise to the refluxing tris-N-(2-aminoethyl-[8-hydroxyquinoline-2-carboxamido])amine/triethylamine solution. The solution was allowed to return to room temperature and the solvent was removed in vacuo to yield tris-N-(2-aminoethyl-[8-hydroxyquinoline-2-carboxamido]) amine indium as a bright yellow-orange solid. MS for $C_{36}H_{30}N_7O_6In$ = 770.9902 g/mole, positive fast atom bombardment, m/e 772 ((M+H)⁺, base peak cation), 660, 558, 458, 369, 329, 299.

EXAMPLE 19

Conjugate Between
N⁴-(2-Aminoethyl-2-(4-Isothiocyanatobenzyl))Tris-N-(8-Hydroxyquinoline-2-Carboxamido)Diethylenetriamine and a Monoclonal Antibody An IgG₁ murine monoclonal antibody specific for carcinoembryonic antigen (CEA) (Abbott Laboratories, North Chicago, Ill.) was dialysed into 0.1M phosphate/0.1M bicarbonate buffer, pH 8.5. The resulting solution was divided into three aliquots. To each aliquot was added a solution of N⁴-(2-aminoethyl-2-(4-isothiocyanatobenzyl))tris-N-(8-hydroxyquinoline-2-carboxamido)diethylenetriamine as the hydrochloride salt in DMSO, such that the first aliquot achieved a final mole ratio of chelator:antibody of 100:1, the second aliquot a mole ratio of 40:1 and the third aliquot a mole ratio of 5:1. All three aliquots were then incubated at 37° C. for 5 hours after addition of sufficient DMSO to produce a homogeneous solution. The resulting solutions were cooled to room temperature and centrifuged to remove any precipitated material. The supernatants were then each dialysed for 48 hours against a 0.05 M solution of DTPA in 0.05 M citrate buffer then for 4 days against multiple changes of 0.05 M citrate buffer, pH 6.0, and finally against 0.1 M borate/0.1 M citrate buffer, pH 10.5.

EXAMPLE 20

Indium-111 Complex of
N⁴-(2-Aminoethyl-2-(4-Isothiocyanatobenzyl))Tris-N-(8-Hydroxyquinoline-2-Carboxamide)Diethylenetriamine and CEA Antibody Conjugate The ability of each of the three antibody-chelator preparations prepared according to Example 19 to specifically bind indium-111 was assessed by instant thin layer chromatography following a DTPA challenge, as described by Meares, et al., Anal. Biochem., 142, 68 (1984). Thus, 500 μCi of indium-111 chloride (New England Nuclear, Billerica, Mass.) was added to 100 μl of each of the three antibody-chelator conjugate solutions, which were then incubated at room temperature for 2 hours. A 20 μl aliquot of each solution was then removed and mixed with 5 μl of a 0.05 M solution of DTPA, pH 6.0. This mixture was incubated at room temperature for 5 minutes then spotted onto silica gel impregnated fiberglass ITLC strips (Gelman Sciences, Ann Arbor, Mich.), which were developed in normal saline. Under these conditions, indium-111 which is specifically bound to chelator sites on the antibody-chelator conjugates remains at the origin, while unbound indium-111 and weakly bound indium-111 that was stripped from the protein by the DTPA elute at the solvent front. Indium-111 activity which remains at the origin of the ITLC strip is thus an indication of stable, specific binding to antibody-bound chelator sites. An untreated aliquot of the same anti-CEA antibody, i.e., an aliquot which had not been conjugated to a chelator, was included as a control. The resulting data appear in Table 1.

TABLE 1

| Preparation | % Applied ¹¹¹In Bound at Origin of ITLC Strip |
|---|---|
| Unconjugated antibody control | 2% |
| 100:1 conjugate | 23% |
| 40:1 conjugate | 12% |
| 5:1 conjugate | 6% |

These data indicate that conjugates were formed between the isothiocyanate chelator of the present invention and the anti-CEA antibody and that the extent of substitution was related to the mole ratio of chelator:antibody employed in the coupling reaction. The data further show that these conjugates were able to specifically bind indium-111 in the face of a challenge with a large excess of DTPA.

From the above examples, it is obvious to those of skill in the art that the conjugates and methods of the invention are useful for imaging of localized concentrations of antigens by external photoscanning such as described in Goldenberg, et al. In such a method, the conjugate is introduced into a patient and the body of the patient is scanned for concentrations of the conjugate. It should also be apparent that the conjugates of the invention may be utilized in vitro diagnostic methods such as immunoassays or nucleic acid hybridization assays. In diagnostic methods such as sandwich hybridization techniques, conjugates according to the invention comprising indicator means are useful in indicating the presence of analytes. Conjugates and methods of the invention are also useful in therapeutic methods wherein an antibody-metal ion conjugate in which the metal ion emits cytotoxic radiation is introduced into a patient such that cytotoxic radiation may be directed to tumors while minimizing the toxic effects to healthy tissues. Chelating agents according to the invention may also be useful for in vivo therapeutic methods both for the administration or removal of radioactive and non-radioactive metal ions. Consequently, only such limitations should be placed on the invention as appear in the following claims.

What is claimed is:

1. A compound characterized by having the structure

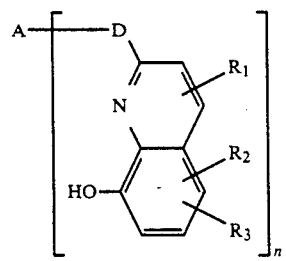

wherein D is selected from the group consisting of

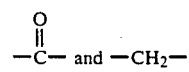

wherein $R_1$, $R_2$ and $R_3$ are the same or different and are selected from the group consisting of hydrogen, halogen, $C_1$-$C_3$ alkyl, nitro, nitroso, sulfonate, sulfo-trialkyl ammonium salts, phosphate, —$CH_2COOH$, —$CH_2CH_2COOH$ and —$CH_2CH_2CH_2COOH$, carboxyamide, sulfonamide, phosphonic acid and sulfate wherein n is 3 or 4 and wherein A is a linear, cyclic or trifurcate tri- or tetraamine wherein the amine nitrogens are linked by alkane, cycloalkane or ortho-substituted phenyl ring substituents having from 2 to 4 carbon atoms between amine nitrogens, the amine nitrogens being positioned such that all of the attendant 8-hydroxyquinoline units are capable of binding a single metal center and wherein A may optionally be substituted at a methylene carbon by the group

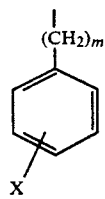

wherein X is meta or para and is a nitro or a substrate reactive moiety and wherein m is 0 to 10.

2. The compound according to claim 1 wherein n is 3.

3. The compound according to claim 1 wherein $R_1$, $R_2$ and $R_3$ are selected from the group consisting of H, OH and sulfonate.

4. The compound according to claim 3 wherein at least one of $R_1$, $R_2$ and $R_3$ is sulfonate and is substituted at the 4 or 5 8-hydroxyquinoline positions.

5. The compound according to claim 1 wherein A is a linear, cyclic or trifurcate tri- or tetraaminoalkane.

6. The compound according to claim 5 wherein A is selected from the group consisting of

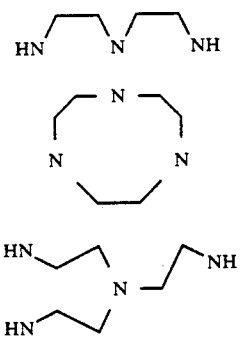

7. The compound according to claim 1 wherein X is selected from the group consisting of:

| | |
|---|---|
| —$NH_2$, | (AMINO) |
| —$NN^+$, | (DIAZONIUM) |
| —NCS, | (ISOTHIOCYANATE) |
| —NCO, | (ISOCYANATE) |
| —$NHNH_2$, | (HYDRAZINE) |
| —$NHCONHNH_2$, | (SEMICARBAZIDE) |
| —$NHCSNHNH_2$, | (THIOSEMI-CARBAZIDE) |
| —$NHCOCH_2Cl$, | (CHLOROACETAMIDE) |
| —$NHCOCH_2Br$, | (BROMOACETAMIDE) |
| —$NHCOCH_2I$, | (IODOACETAMIDE) |
| —$N_3$, | (AZIDE) |
| —$CO_2H$, | (CARBOXYLATE) |
| —$NHCONH(CH_2)_wNH_2$, | (AMINOALKYLUREA) |
| —$NHCSNH(CH_2)_wNH_2$, | (AMINOALKYLTHIOUREA) |
| —$NHCONH(CH_2)_wCO_2H$, | (CARBOXYALKYLUREA) |
| —$NHCSNH(CH_2)_wCO_2H$, | (CARBOXYALKYLTHIOUREA) |
| 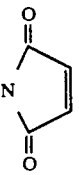 | (MALEIMIDE) |
| ![halotriazine] | (HALOTRIAZINE) and, |
| —NHCSNH—C₆H₄—B(OH)₂ | (META-(DIHYDROXYBORYL)PHENYLTHIOUREA) | wherein Y is selected from the group consisting of Cl, Br and F;

wherein Z is selected from the group consisting of Cl, Br, F, OH and $OCH_3$; and wherein w is 1 to about 10.

8. The compound according to claim 7 wherein X is selected from the group consisting of:
—$NH_2$,
—NCS,
—$NHCSNHNH_2$,
—$NHCOCH_2Br$ and
—$NHCSNH(CH_2)_2NH_2$.

9. The compound according to claim 1 wherein X is para substituted.

10. The compound according to claim 1 wherein m is 1.

11. The compound according to claim 6 characterized by having the structure:

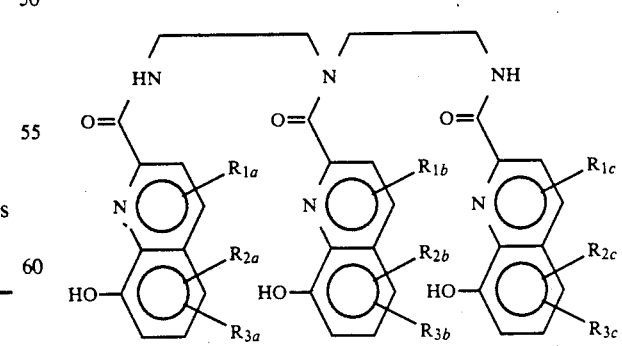

wherein $R_{1a}$, $R_{1b}$ and $R_{1c}$ are the same or different group, wherein $R_{2a}$, $R_{2b}$ and $R_{2c}$ are the same or different group and wherein $R_{3a}$, $R_{3b}$ and $R_{3c}$ are the same or different group.

12. The compound according to claim 6 characterized by having the structure:

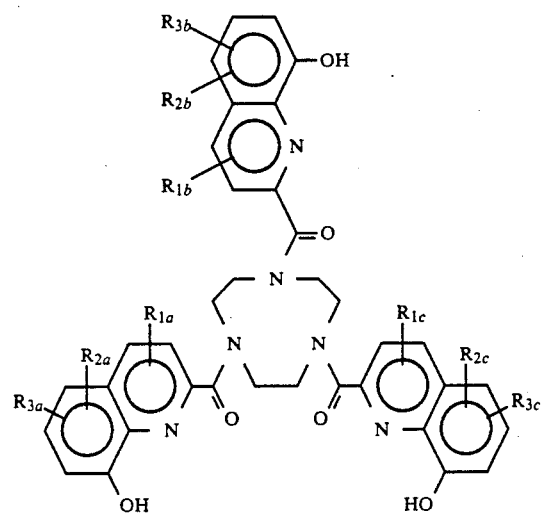

wherein $R_{1a}$, $R_{1b}$ and $R_{1c}$ are the same or different group, wherein $R_{2a}$, $R_{2b}$ and $R_{2c}$ are the same or different group and wherein $R_{3a}$, $R_{3b}$ and $R_{3c}$ are the same or different group.

13. The compound according to claim 6 characterized by having the structure:

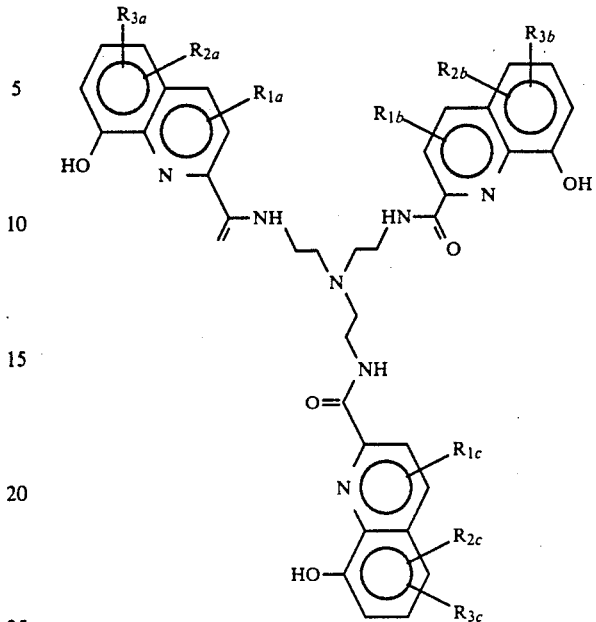

wherein $R_{1a}$, $R_{1b}$ and $R_{1c}$ are the same or different group, wherein $R_{2a}$, $R_{2b}$ and $R_{2c}$ are the same or different group and wherein $R_{3a}$, $R_{3b}$ and $R_{3c}$ are the same or different group.

* * * * *

UNITED STATES PATENT AND TRADEMARK OFFICE
CERTIFICATE OF CORRECTION

PATENT NO. : 5,021,567
DATED : 6/4/91
INVENTOR(S) : D. K. Johnson and S. J. Kline It is certified that error appears in the above-identified patent and that said Letters Patent is hereby corrected as shown below:

Column 3, line 13, change "ironenterobactin" to

--iron-enterobactin--.

Column 15, line 5, change "111Indium" to
    111
--    Indium --.

In the part of the structure formula at column 36, lines 10 to 11, change 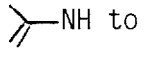 to 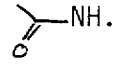.

Signed and Sealed this

Tenth Day of November, 1992

*Attest:*

DOUGLAS B. COMER

*Attesting Officer*          *Acting Commissioner of Patents and Trademarks*